United States Patent [19]

Fetz et al.

[11] 4,104,339
[45] Aug. 1, 1978

[54] METHOD FOR THE MANUFACTURE OF INTRAOCULAR LENSES

[76] Inventors: James G. Fetz, 14930 E. Ramona Blvd., Baldwin Park, Calif. 91706; Ronald P. Jensen, 540 N. Central Ave., Glendale, Calif. 91203

[21] Appl. No.: 637,321

[22] Filed: Dec. 3, 1975

[51] Int. Cl.² .................. B29D 11/00; A61F 1/16; A61F 1/24
[52] U.S. Cl. ............................................. 264/1; 3/13; 264/27; 264/249
[58] Field of Search .......................... 264/1, 25, 27, 248, 264/249; 219/10.73, 10.57, 107; 3/1, 13

[56] References Cited

U.S. PATENT DOCUMENTS

| | | | |
|---|---|---|---|
| 1,784,216 | 12/1930 | Aldrich et al. | 264/248 |
| 2,328,708 | 9/1943 | Cook et al. | 264/27 |
| 2,397,471 | 4/1946 | Cox | 264/25 |
| 2,834,023 | 5/1958 | Lieb | 3/1 |
| 3,265,781 | 8/1966 | Peterson | 264/27 |
| 3,515,777 | 6/1970 | Holthaus | 264/27 |
| 3,820,221 | 6/1974 | Mercer | 264/36 |
| 3,906,551 | 9/1975 | Otter | 3/13 |
| 3,971,073 | 7/1976 | Richards et al. | 3/13 |

FOREIGN PATENT DOCUMENTS

| | | | |
|---|---|---|---|
| 2,000,704 | 8/1971 | Fed. Rep. of Germany | 3/13 |

*Primary Examiner*—James B. Lowe
*Attorney, Agent, or Firm*—T. L. Stam

[57] ABSTRACT

Methods and apparatus are disclosed for the manufacture of plastic intraocular lenses of the type used for transplant in the human eye for natural lens replacement in cataract surgery. The novel methods and apparatus of the present invention are characterized in that the lines or wires used as retention loops are attached to the plastic lens bodies by fusing the ends thereof internally of the lens body in a position remote from the outer peripheries of the lens bodies but outside the central areas of vision of the lens bodies, one method of fusing the ends of the wires to the lens bodies being by heating the wires and pushing them into the lens bodies.

13 Claims, 17 Drawing Figures

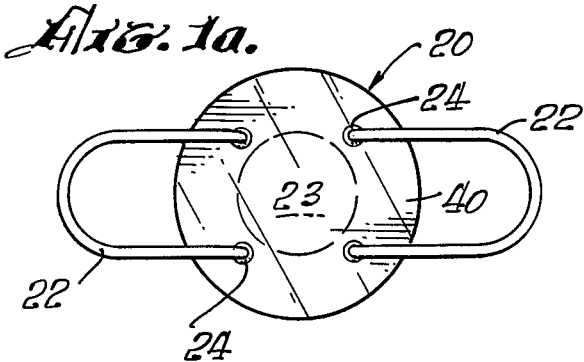
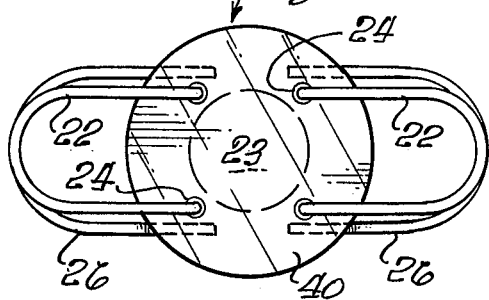
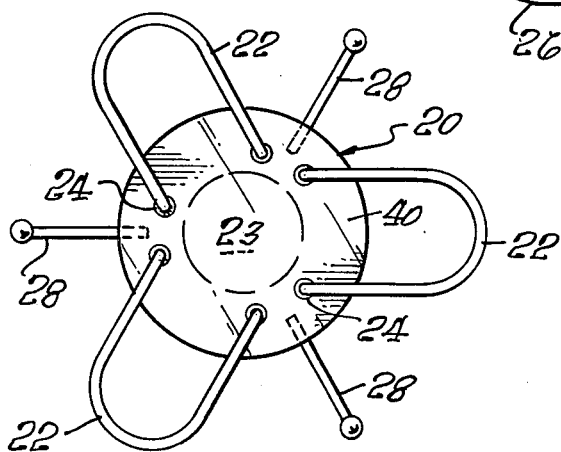
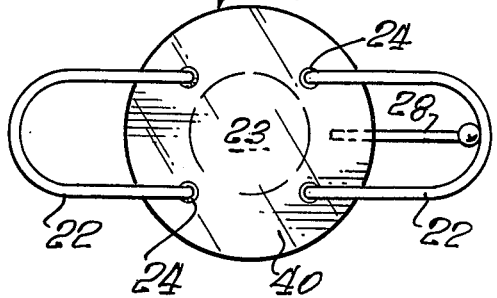
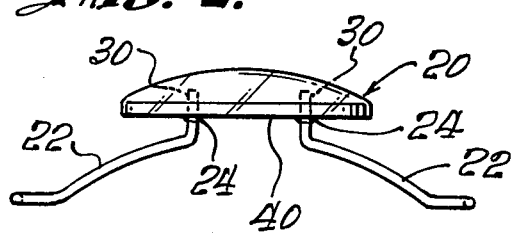

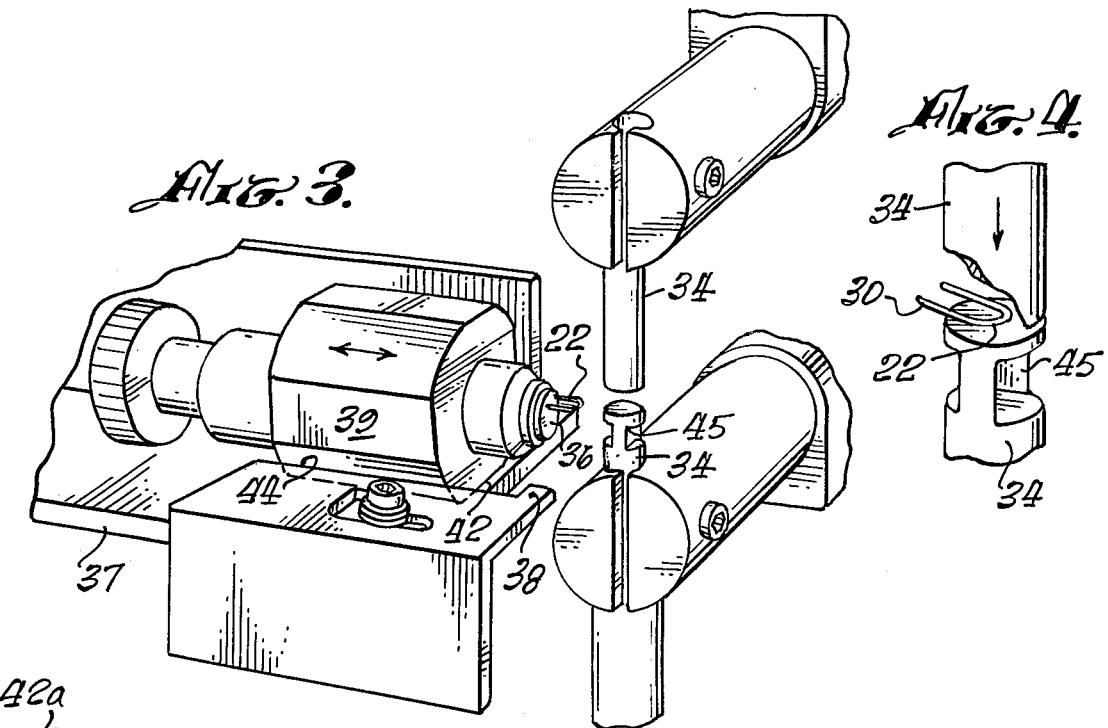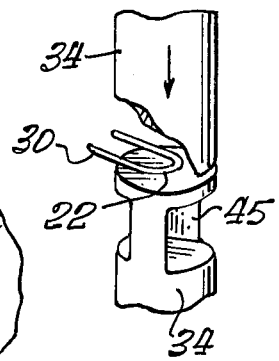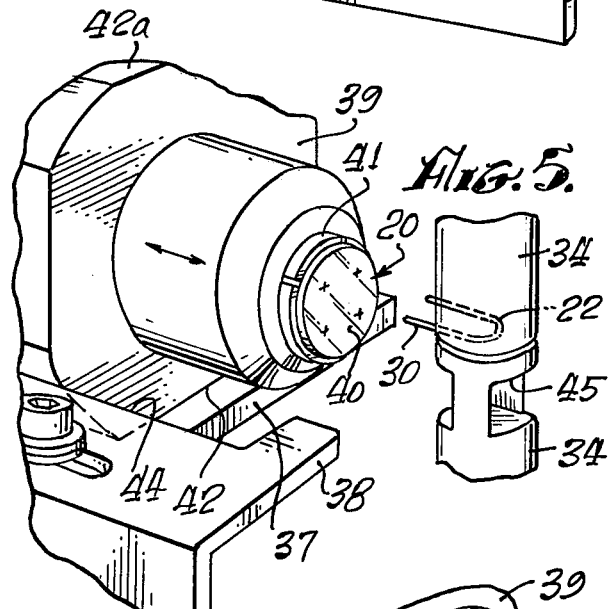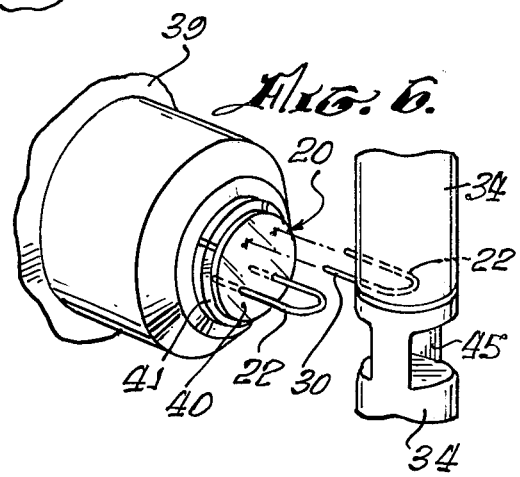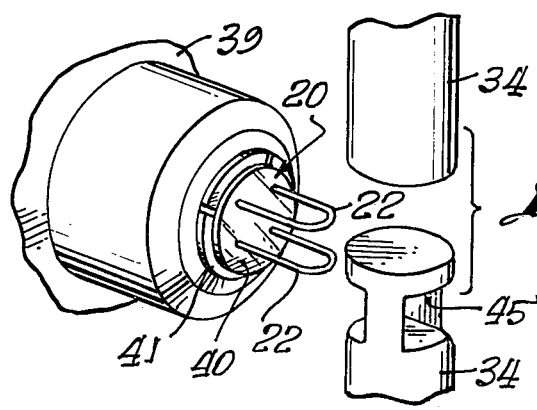

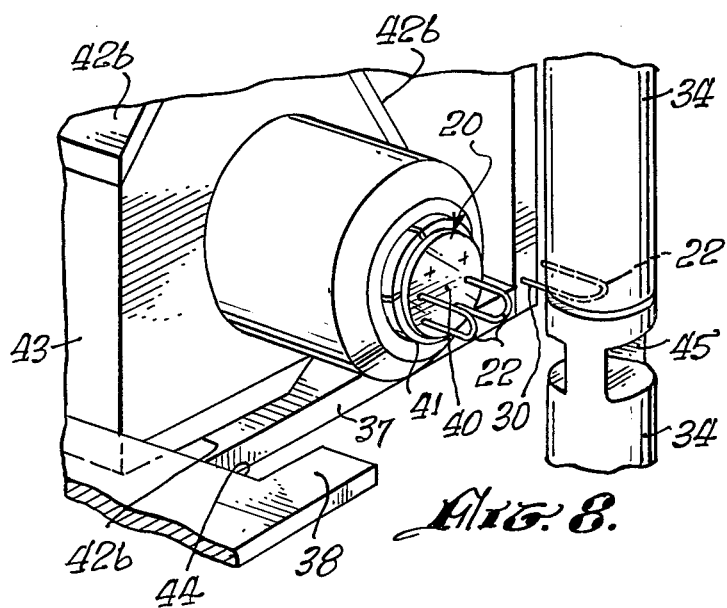
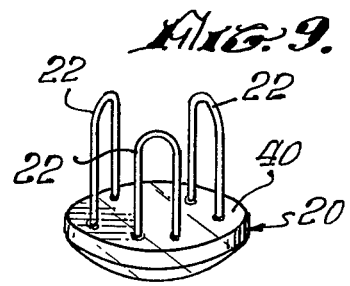
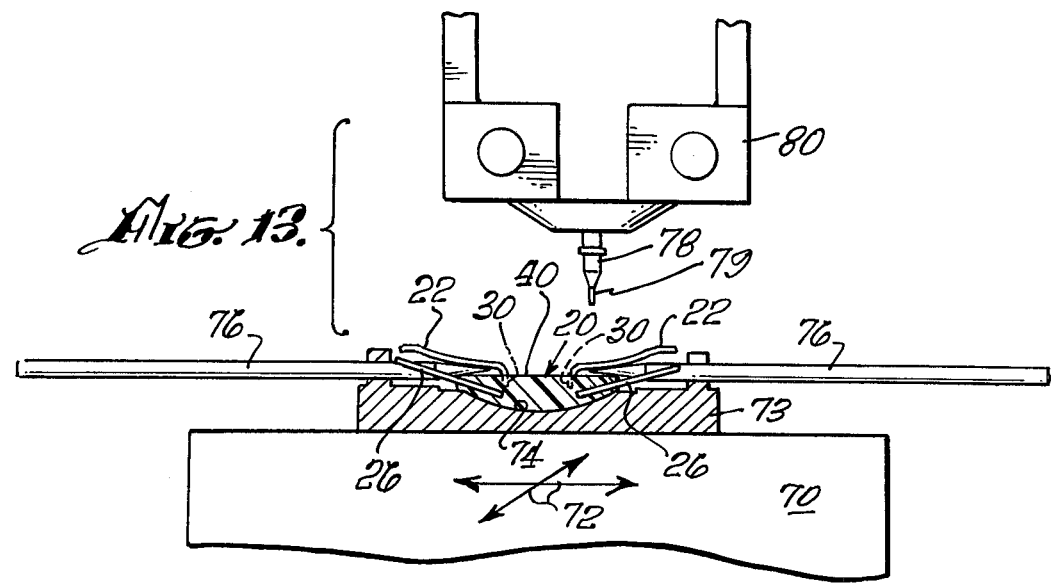
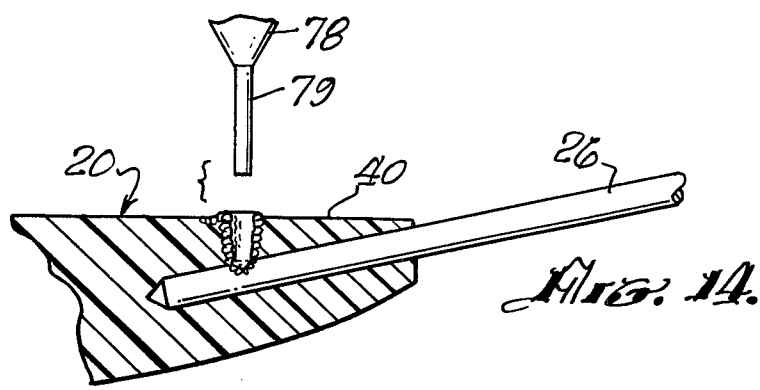

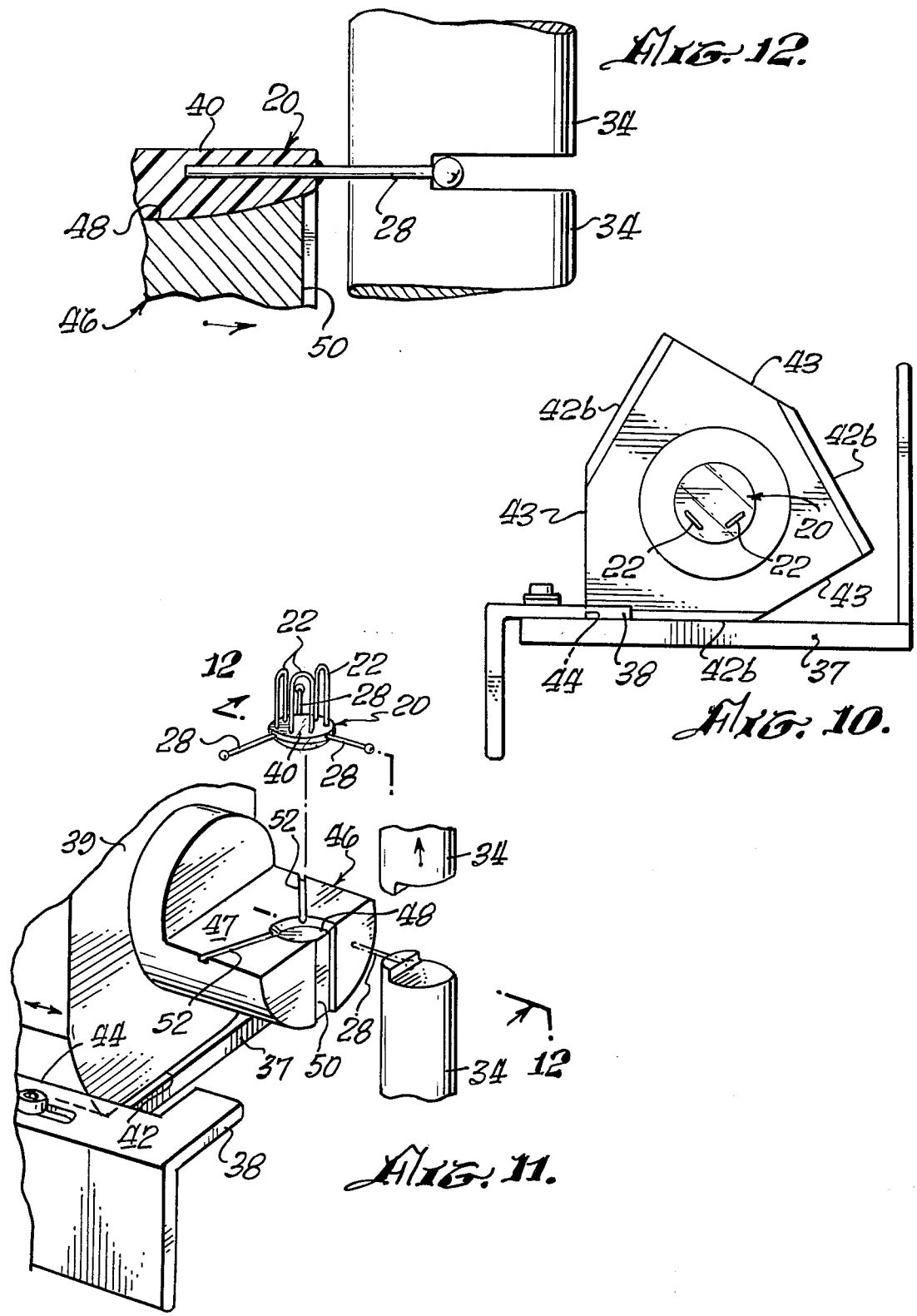

METHOD FOR THE MANUFACTURE OF INTRAOCULAR LENSES

BACKGROUND OF THE INVENTION AND DESCRIPTION OF THE PRIOR ART

At above 1950 intraocular lenses were introduced. Such lenses are man-made, each comprising a plastic lens blank having retention devices attached thereto. They are utilized to replace the natural lenses of patients suffering from cataracts. Thus, in the use of such lenses the diseased natural lens is removed, and, at the same time an intraocular lens is surgically inserted to replace the natural lens. Intraocular lenses are advantageous in that they are optically ideal, because the placement of the artificial lens where the natural lens came from restores the patient to almost normal vision as distinguished from prior cataract operations which simply removed the lens and depended upon heavy cataract glasses or contact lenses to restore vision. The cataract glasses were subject to causing over magnification and distortion such as tunnel vision. Contact lenses are unsuitable for many patients and at best cause some magnification discomforts. For these reasons use of intraocular lenses is of increasing importance in the field of opthalmological surgery. Because of the advantages mentioned herein intraocular lens are coming into more general use and are now a preferred form of surgical treatment for cataracts.

Intraocular lenses are each comprised of a disc of appropriate material, such as a low monomer clear acrylic plastic. One specific example of a medically approved material is polymethylmethacrylate, which is a thermoplastic acrylic suitable for implantation. The plastic disc is carefully machined to an appropriate diameter to fit the lens cavity of the eye and to provide a flat circular base and a convex front face of thickness and curvature to give a lens of desired diopter rating. Such lenses are provided with two or more loops for retention in the eye of the patient and may also be provided with metal locking pins to assist in retention. The loops may be made of thin wires or lines of appropriate metal or plastic material. Typically, metal loops are made of platinum iridium wire and plastic loops are made of thermoplastic material (an approved material is sold under the trade name SUPRAMID).

Although specific dimensions are not critical to understanding or practice of this invention it should be understood that lenses of the type under discussions are quite small, light and delicate. Intraocular lenses are provided with a variety of retention arrangements to provide for patients having different problems. One common type is called the extracapsular lens and is surgically positioned in the patient's eye utilizing capsular fixation. Extracapsular lenses normally have one pair of opposed outwardly disposed loops, generally of metal wire such as platinum iridium and which are designated posterior loops because the ends are attached into and through the rear face or base of the lengs. The four ends of the two loops are generally arranged in a square pattern at distances of about 1 mm. from the center line of the lens, outside the line of vision of the wearer. The loop wires are of 0.15 to 0.20 mm. diameter and extend axially downwardly from the base about 0.6 mm. and are then curved outwardly and downwardly on about a 30 mm. radius curve to about 0.15 mm. from their ends. The length of the overall assembly measured to the ends of the two-loops is 7.5 to 8 mm. A variation is the intracapsular lens which is a four loop lens which is surgically attached by "iris-on-iris" fixation and a loop suture in the iridectomy. The intracapsular lens has all of the structure previously described but is provided with an extra pair of loops, designated anterior loops. These are generally made of plastic line extending from the sides of the lens disc and are positioned concentrically outwardly relative to the posterior loops.

State of the art intraocular lenses are characterized in that all of the loops are attached by press or slip fitting the wires into holes drilled through the lens. In the state of the art lenses, attachment of posterior loops is generally by insertion of the ends of the loops into holes drilled entirely through the lenses from the base toward the face of the lens. Such holes are drilled entirely through the lens from the back surface of the lens through the curved lens face and are beveled or deburred at the ends, the bevelling typically causing material displacement or distortion of an area 3 times the diameter of the iris. Typically, the material of such loops is of a diameter equal to or slightly larger than the diameter of the through-bores and are press or slip fitted into the holes, causing displacement of material in some cases. Two such loops are usually used, providing four ends which are attached, as previously described, generally in a square pattern.

Prior art anterior loops are typically of resilient thermoplastic material, one approved material for this purpose being sold under the trade name "SUPRAMID". A length of line of such material is inserted through two holes drilled through the sides of the lens disc as opposed or parallel chords in the circular periphery of the side walls thereof. Typically two such loops are formed of a single length of line which passes entirely through one of said holes and the ends of which are slip fitted into a butting relationship within the other hole.

Aside from the two specific lens and loop configurations described above, many other configurations have evolved, depending upon either the preferences of surgeons using such lenses or upon particular patient requirements. Thus, as will be better described hereinafter, lenses may have one to four or more loops. Moreover, some lenses are provided with wire extensions having enlarged balls at the ends thereof, called locking pins, such pins being fitted into the side or anterior surfaces of lenses and serving to mechanically lock tissue to loops or to be mechanically embedded in tissue. However, in the prior art, all such attachments, whether loops or pins, were attached by press fitting the wire or other material into pre-bored holes. Prior to the present invention the described press fitting techniques were the only mode available for effecting the connections in intraocular lenses, since glues cannot be used for medical and optical reasons such as the dangers of discoloration, contamination, toxicity and the like.

One disadvantage of all previously described prior art intraocular lenses is instability, i.e. the possibility of press fitted loops and/or pins pulling out in handling during surgery or afterwards. Moreover, the press fits of some loops and/or pins may cause displacement of plastic material, causing distortion, stress risers and possible eventual striations in the lens, which would impair the vision of the wearer. This latter disadvantage is accentuated in the posterior loop structure wherein the ends of metal wires are forced through chamfered through bores of equal or lesser diameter. This reqired mode of assembly causes frizzing of the wire ends and burring of the hole just below the face of the lens. Moreover, the chamfers used to assist assembly and for smoothing causes stress risers which may lead to progressive striation of the lens with increasing impairment of vision. The parent invention relates specifically to improved methods and apparatus for connecting retention loops and locking pins to intraocular lenses of the type described. Reference is made to applicant's prior U.S. patent application, Ser. No. 599,112, filed July 25, 1975, which issued Nov. 30, 1976, as U.S. Pat. No. 3,994,027, disclosing and claiming as articles of manufacture intraocular lenses of types which can be manufactured by the methods and apparatus of the present invention. However, the invention is not intended to be limited as to any specific pin and/or loop arrangement since the gist of the invention is in the apparatus for and methods of effecting the connections of such pins and/or loops to the lenses, whatever the configuration.

OBJECTS AND SUMMARY OF THE INVENTION

Thus, an object of the invention is to provide new and improved methods and apparatus for the manufacture of intraocular lenses.

A further object of the invention is to provide improved methods and apparatus for effecting stronger and more reliable connections of retention loops and/or locking pins to the lens material of intraocular lenses.

Yet another object of the invention is to provide improved methods and apparatus for creating fused connections of pins and/or loops to the plastic material of intraocular lenses without creating heat rings or other distortions of the lens material of an extent to affect the optical quality of such lenses in the area of vision of the wearer.

A still further object of the invention is to provide improved methods and apparatus for effecting fused connections of retention pins and/or loops wherein distortion is equal to or less than that caused by prior art press-fit techniques and in which the stress risers and surface deformation inherent in such techniques are obviated.

The above and other objects of the invention are derived by providing novel methods and apparatus for fusing the ends of pins and or loops to either the posterior or anterior surfaces of the lens material in a manner to minimize optical distortion of the lens material, as by heat rings or material displacement or the like, thus overcoming the disadvantages of weak mechanical strength and danger of further optical distortion prevalent in the prior art. These and other objects and advantages of the invention will become better understood by reference to the following detailed description when considered in conjunction with the accompanying drawings, wherein like reference numerals have been applied to like parts throughout.

BRIEF DESCRIPTION OF THE DRAWINGS

FIGS. 1(a), (b) (c) and (d) are elevation schematic views of typical intraocular lens configurations illustrating some arrangements of pins and/or loops utilized for retention of such lenses to the tissues of the eye.

FIG. 2 is a side elevation of a lens similar to that of FIG. 1(a), as made by the methods of the present invention.

FIGS. 3 and 4 are perspective views illustrating a means for positioning or loading a metal loop wire in a clamp for formation of a posterior loop by attachment of the loop ends into the base of a lens body.

FIG. 5 is a perspective view illustrating means for effecting a fused connection of a loop wire as shown in FIGS. 3 and 4 into the flat base of a plastic lens body.

FIGS. 6 and 7 are perspective views illustrating means for and the method of positioning and clamping and effecting a fused connection of the second of a pair of posterior loops in the manufacture of a two-loop extracapsular intraocular lens, as shown in FIG. 1(a) according to this invention.

FIG. 8 is a fragmentary perspective view illustrating an arrangement for attaching three posterior loops to the base of a plastic lens according to this invention.

FIG. 9 is a perspective illustrating a lens body having three posterior loops attached thereto, as by the apparatus and method shown in FIG. 8.

FIG. 10 is an end view of the chuck and guide block of FIG. 9, illustrating the guide block configuration.

FIG. 11 is a fragmentary, exploded perspective view of an arrangement for attaching locking pin elements into the side or anterior walls of intraocular lens bodies.

FIG. 12 is a fragmentary, enlarged sectional view taken along the line 12—12 of FIG. 11.

FIG. 13 is a fragmentary sectional view illustrating the method of attaching anterior loops of the type chown in FIG. 1(b).

FIG. 14 is an enlarged fragmentary sectional view of an anterior loop connection made by the method and apparatus illustrated in FIG. 13.

DESCRIPTION OF THE INVENTION

As a prelude to description of the present invention it is considered that illustration of some typical intraocular lens configurations is necessary. FIGS. 1(a), 1(b), 1(c) and 1(d) schematically illustrate some typical arrangements, and FIG. 2 illustrates the nature of fused connections according to the invention. All configurations utilize similar lens bodies 20 which comprise a ground and polished rounded front face and a flat-backed base position and are of a size and configuration to fit the lens cavity of the eye. Moreover, all of the illustrated configurations include at least two loops 22 of the type designated posterior loops in the previous description.

Thus, FIG. 1(a) illustrates the extracapsular lens previously described, having a pair of wire loops 22 attached through the posterior surface or base of the lens body 20. It should be noted that whether by the drilling, bevelling, and press fitting technique of the prior art or by the fusing techniques of the present invention, an area of optical distortion 24 is permissible which is of the order of three times the diameter of the wire and which is still outside the viewing area of the wearer which is shown in dotted lines and designated by the reference numeral 23 in FIGS. 1(a), (b), (c) and (d).

FIG. 1(b) illustrates the previously described intracapsular lens which has, in addition to posterior loops 22, a second pair of loops 26 attached into the side wall of the lens body and designated anterior loops. In the prior art, a single length of the plastic line is drawn entirely through one through bore and the ends thereof butted against one another in an opposed parallel through bore, in a press fit, to form the two loops. The showing of FIG. 1(b) is illustrative of anterior loops 26 formed, according to this invention, of two lengths of plastic line, the ends of each length being fused in holes not extending entirely through the lens material, as will be described in detail hereinafter.

FIGS. 1(c) and 1(d) are illustrative of two arrangements which utilize metallic locking pins 28 in combination with several posterior loop arrangements. In the FIG. 1(c) arrangement an enlarged ball is mechanically engageable with the outer end of one of the posterior loops to effect a mechanical locking of tissue. In the FIG. 1(d) arrangement, the enlarged balls of the plurality of locking pins are embedded in eye tissue to give additional holding function to the assembly. As shown, each locking pin constitutes a metal pin or rod, having an enlarged end, as shown. They, like posterior loops 22, are typically of platinum iridium wire and the main length thereof may be of the same diameter (0.15 to 0.20mm) as the wire used in the posterior loops described herein. In the prior art such pins were attached by drilling holes to receive them, the holes and wire being of such diameter as to provide a slip or press fit.

The present invention provides methods and apparatus for effecting improved connections of the type discussed for all of the types of retention devices shown in FIGS. 1(a) (b) (c) and (d). The improved connections can withstand tensions of 4 ounces (as compared to one ounce for press fitted connections) and are mechanically and optically advantageous in that the frizzed loop and pin ends and the scratching of lens material with the attendant stress riser problems of the prior art practices are obviated.

In a general sense the present invention involves carefully controlled melting of the thermoplastic lens material to cause fusion thereof to the material of loops or pins of the type described, all in such a manner as not to distort the lens material in the optical viewing area of the pupil of a wearer or to create stress risers or scratches which might lead to later optical deterioration in use.

It is therefore essential to practice of this invention that the heating and attachment procedures not produce heat rings in the lens material of an extent to enter the viewing area or otherwise cause displacement of material in such areas. Typically, each of the types of attachment herein described is made, according to the present invention, by apparatus and methods in which heat is applied to melt the lens material in such a manner that such material is melted or heat rings formed over areas not exceeding three times the diameter of the material of the attachement, outside the viewing area 23, and that there is no other displacement of lens material into the viewing area, and not requiring openings in the rounded front faces of the lenses (see FIG. 2).

The novel result is achieved, as to posterior loops, by heating the wires of which the loops are made to a temperature slightly above the melting temperature of the lens body material and pressing the ends of the wire into the lens body. In this manner, the lens body material is melted only in the direct vicinity of the wire ends, and, upon cooling, forms relatively strong fused connections with such wire ends.

FIGS. 3 to 8 illustrate the methods and apparatus for attaching several configurations of posterior loops according to the present invention. In the practice of the present invention the wire used for a posterior loop, in appropriate precut length, is clamped in a manner to expose the ends a desired distance and spaced from one another a desired distance. While specific dimansions are not a limitation of the present invention, typical dimensions will be given, since the small dimensions involved relate to the problem solved. Thus, the wire length for typical posterior loops is about 12.0 mm, the exposed portion 30 intended to be embedded in a fused connection in the lens body is 0.4 mm and the wire ends are disposed 2.0 mm apart. The length of the loop and the spacing of wire ends from one another are dictated by the more or less standard circumferential dimensions of lenses of the type under discussion and by the requirement that connections be as far from the periphery of the lenses as possible, but that distortions due to the connection be outside the viewing area of the wearer. Thus, referring to FIG. 6, the embedded ends 30 of the two opposed loops must be sufficiently outside the viewing area, designated 23 and shown in dotted lines, so that heat rings 24 or other distortion will not encroach upon the viewing area.

Similarly, and specific to this invention, the advantages of unbroken and smooth surfaces of lenses are preserved by limiting the extent of insertion, as shown (see FIG. 2). Typically, but not as limitations to this invention, the lens blanks are 0.65 mm in thickness at the thickest point and, for such lenses posterior loop wire ends are inserted about 0.4 mm, whereby the procedures outlined herein permit relatively strong connections to be made without material flow causing bumps or distortion on the faces of the lenses and with heat rings, if any, too small to extend into the viewing area.

Referring now to FIGS. 3 to 8, a loop wire 22 may be positioned in clamp jaws 34 by inserting its ends 30 into openings in the face of a gauge block 36, as shown in FIG. 3, which are of desired spacing. The block may be placed by hand in the clamping means but it is preferred to support it in a suitable chuck 39 and guide it on a work bench 37 at a desired height and to provide a stop, as at 38, and a guide 44, to accurately define the position of the loop relative to the clamping jaws 34, particularly the length of loop to be held within the clamping jaws and the length exposed (for insertion into the lens body). Once the loop is so positioned the clamping elements 34 are actuated to grip the loop (see FIGS. 4, 5, 6 and 8) and the gauge block withdrawn (see FIG. 4).

A lens blank, previously ground and polished, is then positioned in a collet 41, the flat base surface 40 exposed. The collet body is of a size and positioned in chuck 39 so that when the flat bottom 42 of the chuck is resting on the work table 37, movement towards the stop 38 along the guide 44 will cause the ends 30 of loop wire 22 held in the clamp jaws 34, to touch the surface 40 of the lens body in desired positions outside the viewing area, the stop 38 being adapted to limit the degree of entry of loop ends 30 into the material of the lens body, as will be described.

With the parts in the position shown in FIG. 5, the clamped loop 22 is heated, instantaneously, by inductive heating or the like by passing electricity through the clamp jaws to cause inductive heating of the wire material of the loop. The degree of heating is controlled so that the temperature of the wire loop reaches a temperature only slightly above the melting point of the plastic material of the lens body. While this temperature may vary for different materials, a typical example is a temperature of about 190° F. when the lens body material is polymethylmethacrylate. While the wire material of the loop is thus being heated, the chuck 39 is pushed toward the clamp, along guide 44, until it engages the stop 38, the heated wire melting adjacent plastic material and entering the lens body the desired distance. When the penetration is completed and the clamp released, the attachment of the loop is completed upon cooling of the melting material about the loop wire ends.

The chuck body is then removed, with the lens body still held in the collet therein. A second loop wire is positioned in the clamp, as previously described (see FIG. 4). The chuck is then rotated 180° so that its opposite guide face 42a rests upon the work table. The induction heating and insertion procedures are then repeated to fuse the second loop to the lens body (see FIGS. 6 and 7). It should be noted that one of the clamp members (the lower in the illustrated example) is provided with a cavity, as at 45. As may be seen in FIGS. 3 to 8, the purpose of the cavity is to accommodate the first attached loop, without deformation, during the process of attaching the second loops 22.

In instances where three loops may be required, as in the FIG. 1(d) configuration, a chuck body may be provided, as shown in FIG. 8, which has three guide faces disposed at 60 degree spacing, as designated by reference numeral 42b. In order to reduce the necessary size of the chuck body and to provide right angle edges for engagement by the guide 44, the faces 42b may be truncated, as at 43, at right angles (see FIGS. 8 and 10). The same procedures previously described are followed to fuse the three loops to the lens body, the cavity in the lower jaw of the clamp 34 being of sufficient size to accommodate previously attached loops. It should be noted that these procedures leave the loops extending axially of the lens body from the base portion thereof. If no further attachments are to be made, the loops are then bent to the final desired configuration described hereinabove.

Locking pins 28, as shown in FIGS. 1(c) and 1(d) are of metal and are fused into the lens bodies, when desired, by the same method described in connection with the fused connection of loop ends 30 above. However, such pins are attached into the lens body anterior or side wall. Clamping jaws 34, suitably surfaced to accommodate the enlarged ball at the ends of the locking pins, as shown in FIG. 12, are utilized to clamp a pin with the free end exposed a desired distance. A chuck is utilized to support a lens blank in a manner to present a side or anterior wall toward the clamp, as shown in FIG. 11. As in the case of posterior loop attachment, the clamp jaws (and locking pin) are heated and the lens blank pushed against the heated locking pin end to cause controlled melting of the lens body material result in a fused connection of the locking pin to the lens body upon cooling.

Obviously, many lens holding arrangements are possible for holding the lenses in a manner to present the anterior walls thereof toward the clamping jaws for effecting connection of locking pins or similar devices into such walls. One such arrangement is shown in FIG. 11 and is adapted for use in attaching either the single locking pin of the FIG. 1(d) configuration or the three locking pins of FIG. 1(c). It comprises a sliding chuck body 39 in which a lens holding tool 46 is supported. Lens holding tool 46 is provided with a flat surface 47 having a cavity 48 of a shape and size to support a lens body with its rounded face down and its flat base facing upwardly. The previously attached loops 22 may therefore extend upwardly from the cavity and the lens base (see FIG. 11). The front face of the lens holding tool is relieved, as at 50, so that the side wall of a lens held in the cavity 48 may contact the surface of the clamp for effecting attachment of the locking pin into the side wall. Two straight grooves 52 are provided spaced 120° from one another and from said relieved portion 50, extending radially outwardly from the center of the lens holding cavity, as shown in FIG. 11. Means, not shown, may be provided to press downwardly on the lens base to hold it securely in the cavity.

A lens which has previously had posterior loops 20 attached thereto is positioned in the cavity 48 with the rounded face down and the loops extending upwardly. For completion of the FIG. 1d configuration, a lens which has had two posterior loops attached to it (as in FIG. 1a) is oriented so that the center of the space between the ends of one of the loops is aligned with the center of the relieved space 50. A wire locking pin 28 is then positioned in the clamp jaws as previously described, and illustrated in FIGS. 10 and 11. The clamp jaws are then subjected to current to inductively heat the locking pin as the chuck and holding tool are advanced along guide 44 to the stop 38 to attach the locking pin in place. The lens is then removed from the cavity 48 and the loops bent into their ultimate shape as previously discussed.

The configuration of FIG. 1c is made by positioning a lens blank to which three posterior loops have previously been attached (see FIGS. 8 and 9) in the cavity 48 in lens holding tool 46 in such a manner that a locking pin 28 may be inserted in the anterior wall of the lens midway between adjacent loops in the manner previously described. After the first such locking pin has been attached the lens is rotated 120 degrees so that the previously attached pin rests in a groove 52. The second locking pin is then attached, and the lens again rotated for attachment of the third locking pin to complete the assembly. FIG. 10 illustrates these procedures.

Attention is now directed to FIG. 1(b) as illustrative of an intraocular lens configuration which includes anterior loops, e.g. loops formed of plastic line and attached into the side walls of the lens bodies, as shown at 26 in FIG. 1(b). FIGS. 13 and 14 illustrate an apparatus for and a technique for attachment of such loops to lens bodies. Thus, four holes of a size to snugly receive the thermoplastic line are drilled into the side walls of the lens body. They are along parallel opposed chords of the lens body, outside the viewing area 23 of the lens. Contrary to the prior art the holes are drilled a depth less than half way through the lens body so that walls of lens material are left between the opposed inner ends of the two separate loops (see FIG. 1(b) and FIG. 14. Also, it is possible, according to this invention, to insert the loop ends angularly into the lens body rather than in lines parallel to the base of the lens body as required by the prior art practices (see FIG. 14), thus permitting rooting of the fused loop ends deeper into the lens body material for greater strength and achieving fixation angle of loops per opthalmologist's specification and achieving a desired angle of fixation as desired by the opthalmologist without requiring bending of the loop line and consequent problems caused by the "memory" of the resilient thermoplastic line, i.e. its tendency to return to a straight configuration.

The fused connection of the plastic line ends to the lens body is made, according to this invention, by applying heat to the lens material in the vicinity of the line ends to cause melting of such material and fusing thereof to the loop line ends. This is accomplished by pushing an inductively heated thin probe through the base 40 of the lens body into contact with the loop line material, as shown in FIGS. 13 and 14. The probe is heated in a manner to heat the lens material to a temperature slightly above the melting point of the lens body material and the probe is gently pushed into its inner position so that only material in the immediate vicinity of the probe entry path is melted and the resulting heat ring is no more than three times the diameter of the probe (and of the loop material). Moreover, such procedures prevent flow of material outside the desired area and prevent surface distortions or bumps on lens surfaces. Typically a temperature of 190° F has been shown to be suitable for polymethylmethacrylate lens bodies and "Supramid" anterior loop material. It should be noted that the relative melting temperatures of the loop and lens materials are not critical, since the fused connection may be formed by the flow of the lens material alone. Generally, however, the materials are of substantially similar melting point, and such a relationship is preferable.

One apparatus for performing the method discussed in the preceding two paragraphs is shown schematically in FIGS. 13 and 14 and comprises a work table 70 of fixed height, movable in any direction by the operator, as schematically indicated by arrows 72, by controls, not shown. The table is provided with a lens holder 73 having a cavity, as at 74, shaped to hold a lens blank with its curved face down and its base portion 40 exposed. The cavity 74 preferably has provision for accommodating both the previously attached and shaped posterior loops 22 and the anterior loop lines 26 which have been positioned in the drilled holes in the side walls of the lens body but not yet fused to the material thereof (see FIG. 13). The lens holder may be provided with side openings to receive pointed hold-down elements 76 which extend through said holes and over the edges of the lens body to hold it in position in the cavity 74. An electrically heatable probe 78 having a thin point 79 of diameter no greater than the diameter of the loop line is mounted above the lens holder for vertical movement relative thereto and may be provided with a microscope, not shown, so that the operator may closely control the probe path relative to the lens body and the ends of the loops 26. Means, not shown, are provided for raising and lowering, and for limiting the downward extent of movement of probe point 79 and an inductive heating means 80 is provided for heating the probe to desired temperatures. It is pointed out that the movable work table and the inductive probe heating and moving means are commercially available state-of-the-art devices, the details of which are not a part of this invention.

In practice, a lens body which has had four holes drilled in the side walls to receive the four ends of the posterior loops 26 is provided and the four loop ends are positioned in the holes. The lens body is then placed in the cavity 74 of lens holder 73 and locked in place by the needle like elements 76 (see FIGS. 13 and 14). The operator, using a microscope, then manipulates the movable work table 70 to position the probe point 79 directly over one of the loop ends, a short distance from the terminal end thereof. Then, as a heating cycle is initiated, as by an induction heater 80, the probe is pushed through the lens base into contact with the material of the loop 26, as shown in FIG. 14. Material of the lens body is melted only in the vicinity of probe entry and of the plastic wire end, and flows around the wire end (see FIG. 14). Upon cooling a fused connection, as discussed hereinabove, is formed. The operation is repeated four times to connect the four ends of two anterior loops 26 to the lens body to complete, for example, the fabrication of the FIG. 1(b) configuration. The application of such techniques to the materials and configurations used in the manufacture of intraocular lenses, of which some examples are given herein, are all characterized in (1) that the finished connections are all fused connections formed by melting of lens body material and cooling of such material on and about the material of the attachment to form the fused connection therewith; and (2) in that the melting of the lens body material is accomplished by heating to temperatures only slightly above the melting point of the lens material and in only limited areas adjacent the attachment material and/or outside the viewing area to minimize displacement of lens body material or the formation of heat rings to an extent no greater than three times the dimension of the material of the attachment and outside the viewing area of the wearer of the lens.

The invention is not intended to be limited in any respect as to the nature of the materials used and specific temperatures required thereby, or the nature of the particular combination of attachments which might be made to the lens body of intraocular lenses of the type described. Rather, the scope of the invention is to be determined by the language and scope of the appended claims.

What is claimed is:

1. A method for connecting an attachment to the material of a thermoplastic intraocular lens body, said attachment being comprised of a length of thin metal line or wire, the method comprising the steps of providing a thermoplastic intraocular lens body having a central area constituting an area of vision and a surrounding area outside said area of vision; providing an attachment in the form of a length of thin metal line or wire adapted to be attached to said lens body; positioning at least one end of the attachment internally of said lens remote from the outer periphery of said lens body and outside said area of vision, heating said material to its melting point only in the vicinity of said at least one end; said steps of positioning at least one end of the attachment internally of the lens body and of heating said material to its melting point being performed simultaneously, by applying heat to said metal attachment to raise its temperature and pushing said at least one end into the material of the lens body, whereby the material of the lens body in the vicinity only of the said at least one end is melted to permit positioning of said at least one end in said lens body and whereby upon cooling, said material forms a fused connection with said attachment.

2. The method of claim 1, further including the steps of positioning said attachment between the jaws of a clamp, with a predetermined length of said at least one end exposed from the clamp to limit the degree of insertion of the at least one end of the attachment into the material of said lens body, the heat being applied to said attachment by heating said clamp.

3. The method of claim 2, wherein said attachment is substantially of a single straight length, one end thereof being positioned in and fused to the material of the lens body.

4. The method of claim 3, wherein the jaws are the electrodes of an induction heater and said attachment is heated by inductive heating.

5. The method of claim 2, wherein said attachment is a loop, the two ends thereof being positioned in and fused to the material of the lens body.

6. The method of claim 5, wherein the jaws are the electrodes of an induction heater and said attachment is heated by inductive heating.

7. A method for connecting a plurality of metal attachments to the material of a thermoplastic intraocular lens body, comprising the steps of providing a thermoplastic intraocular lens body having a central area constituting an area of vision and a peripheral area outside said area of vision; providing an attachment in the form of a length of thin line or wire adapted to be attached to said lens body; clamping said attachment between the electrodes of an induction heater with at least one end thereof exposed a predetermined distance; positioning said lens body in a chuck with a surface thereof exposed; inductively heating said attachment; and moving said chuck relatively towards said clamp a predetermined distance whereby said at least one end melts the material of the lens body and penetrates said body a predetermined distance; said clamped attachment being aligned relative to said chuck so that said penetration occurs remote from the outer periphery of said lens body and outside said area of vision; loosening said electrodes; removing said chuck; and allowing said attachment and lens body to cool; rotating said lens body to position a desired second surface in position to receive the at least one end of a second attachment, and repeating said clamping, positioning, heating, insertion, electrode loosening and removal and cooling steps to effect connection of a second attachment to said lens body.

8. The method of claim 7, wherein the attachments are locking pins having thin wire bodies and enlarged exterior ends, the interior ends being intended for connection into the anterior surface of said lens bodies, the lens body being held in the chuck with the anterior surface disposed for relative movement towards and away from the electrode clamp jaws, said lens body being rotated to present a desired different portion of the side surface toward said electrode clamp jaws for each of the plurality of locking pins to be attached thereto.

9. The method of claim 7, wherein the attachments are loops each having two ends thereof intended for attachment into the base of the lens body, the lens body being held in a chuck with the base thereof disposed for relative movement towards and away from the electrode clamp jaws, said chuck being rotated to present a different desired portion of said base toward said electrode clamp jaws for each of the plurality of loops to be attached thereto.

10. A method for connecting an attachment to the material of a thermoplastic intraocular lens body, said attachment being comprised of a length of thin line or wire, the method comprising the steps of providing a thermoplastic intraocular lens body having a central area constituting an area of vision and a peripheral area outside said area of vision; providing an attachment in the form of a length of thin line or wire adapted to be attached to said lens body; positioning at least one end of the attachment internally of said lens body outside said area of vision, heating said material to its melting point only in the vicinity of said at least one end; and allowing the melted material to cool, whereby to form a fused connection between said material and said attachment, the steps of positioning at least one end of the attachment internally of said lens body comprising drilling a pair of spaced holes into the anterior surface of said lens body along parallel paths spaced on opposite sides of and exterior to said area of vision and less than half way through said lens body and placing the two ends of the attachment into said holes; the heating of said material comprising the positioning of a heatable probe outside the base of said lens body in alignment with one of said ends positioned in one of said holes; heating said probe and moving it into and through the base of said lens body into contact with one of said two ends by melting the lens body material from the base through to said end and melting the material adjacent said end; removing said probe; repositioning said probe in alignment with the second of said ends positioned in the other of said holes; heating said probe and moving it into and through the base of said lens body into contact with said second end; and removing the probe and allowing the attachment and lens body to cool whereby to form a loop attachment having two ends fused to the material of the lens body.

11. The method of claim 10 wherein the probe is heated by inductive heating.

12. The method of claim 10 wherein the attachment is of thermoplastic material.

13. The method of claim 10 further characterized in that a second loop is attached in the same manner as the said first loop, with its inner ends spaced from and opposed to the inner ends of said first loop.

* * * * *

Disclaimer

4,104,339.—*James G. Fetz*, Baldwin Park and *Ronald P. Jensen*, Glendale, Calif. METHOD FOR THE MANUFACTURE OF INTRAOCULAR LENSES. Patent dated Aug. 1, 1978. Disclaimer filed Feb. 7, 1984, by the *inventors*.

The term of this patent subsequent to Nov. 30, 1993, has been disclaimed.
*[Official Gazette May 15, 1984.]*